United States Patent [19]
Fisher et al.

[11] Patent Number: 5,714,506
[45] Date of Patent: Feb. 3, 1998

[54] SELECTIVE $\beta_3$ AGONISTS FOR THE TREATMENT OF DIABETES AND OBESITY

[75] Inventors: Michael H. Fisher, Ringoes; Hyun O. Ok, Edison; Ann E. Weber, Scotch Plains, all of N.J.

[73] Assignee: Merck & Co., Inc., Rahway, N.J.

[21] Appl. No.: 717,659

[22] Filed: Sep. 23, 1996

Related U.S. Application Data

[60] Provisional application Nos. 60/006,070, Oct. 24, 1995, and 60/004,332, Sep. 26, 1995.

[51] Int. Cl.$^6$ .................... A61K 31/44; C07D 213/30
[52] U.S. Cl. .................... 514/352; 514/357; 546/309; 546/312; 546/334
[58] Field of Search .................... 546/309, 312; 514/334, 352, 357

[56] References Cited

U.S. PATENT DOCUMENTS

| | | | |
|---|---|---|---|
| 4,358,455 | 11/1982 | Alkinson et al. | 424/263 |
| 4,396,627 | 8/1983 | Ainsworth et al. | 424/309 |
| 4,800,206 | 1/1989 | Alig et al. | 514/332 |
| 4,816,457 | 3/1989 | Baldwin et al. | 514/256 |
| 4,863,939 | 9/1989 | Lindel et al. | 514/357 |
| 4,906,645 | 3/1990 | Fisher et al. | 514/352 |
| 5,561,142 | 10/1996 | Fisher et al. | 514/312 |

FOREIGN PATENT DOCUMENTS

| | | |
|---|---|---|
| 0 659 737 | 6/1995 | European Pat. Off. . |
| 56-55369 | 5/1981 | Japan . |
| WO 94/29290 | 12/1994 | WIPO . |
| WO 95/29159 | 11/1995 | WIPO . |

OTHER PUBLICATIONS

Bobowski et al, J. of Heterocyclic Chemistry, vol. 19, No. 1, Jan.–Feb., 1982, pp. 21–27.

*Primary Examiner*—Zinna Northington-Davis
*Attorney, Agent, or Firm*—Mollie M. Yang; David L. Rose

[57] ABSTRACT

Compounds of formula

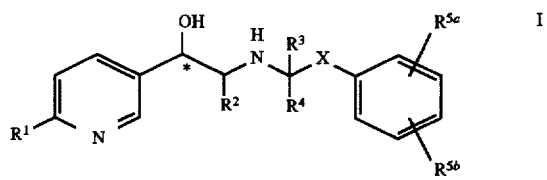

are selective $\beta_3$ adrenergic receptor agonists with very little $\beta_1$ and $\beta_2$ adrenergic receptor activity and as such the compounds are capable of increasing lipolysis and energy expenditure in cells. The compounds thus have potent activity in the treatment of Type II diabetes and obesity. The compounds can also be used to lower triglyceride levels and cholesterol levels or raise high density lipoprotein levels or to decrease gut motility. In addition, the compounds can be used to reduced neurogenic inflammation or as antidepressant agents.

17 Claims, No Drawings

SELECTIVE β₃ AGONISTS FOR THE TREATMENT OF DIABETES AND OBESITY

RELATED APPLICATIONS

This application claims priority to U.S. provisional application Ser. No. 60/006.070, filed Oct. 24, 1995, and to U.S. provisional application Ser. No. 60/004,332, filed Sep. 26, 1995.

BACKGROUND OF THE INVENTION

β-Adrenoceptors have been subclassified as $\beta_1$ and $\beta_2$ since 1967. Increased heart rate is the primary consequence of $\beta_1$ receptor stimulation, while bronchodilation and smooth muscle relaxation typically result from $\beta_2$ stimulation. Adipocyte lipolysis was initially thought to be solely a $\beta_1$-mediated process. However, more recent results indicate that the receptor-mediating lipolysis is atypical in nature. These atypical receptors, later called $\beta_3$-adrenoceptors, are found on the cell surface of both white and brown adipocytes where their stimulation promotes both lipolysis (breakdown of fat) and energy expenditure.

Early developments in this area produced compounds with greater agonist activity for the stimulation of lipolysis ($\beta_3$ activity) than for stimulation of atrial rate ($\beta_1$) and tracheal relaxation ($\beta_2$). These early developments disclosed in Ainsworth et al., U.S. Pat. Nos. 4,478,849 and 4,396,627, were derivatives of phenylethanolamines.

Such selectivity for $\beta_3$-adrenoceptors could make compounds of this type potentially useful as antiobesity agents. In addition, these compounds have been reported to show antihyperglycemic effects in animal models of non-insulin-dependent diabetes mellitus.

A major drawback in treatment of chronic diseases with $\beta_3$ agonists is the potential for stimulation of other β-receptors and subsequent side effects. The most likely of these include muscle tremor ($\beta_2$) and increased heart rate ($\beta_1$). Although these phenylethanolamine derivatives do possess some $\beta_3$ selectivity, side effects of this type have been observed in human volunteers. It is reasonable to expect that these side effects resulted from partial $\beta_1$ and/or $\beta_2$ agonism.

More recent developments in this area are disclosed in Ainsworth et al., U.S. Pat. No. 5,153,210, Caulkett et al., U.S. Pat. No. 4,999,377, Alig et al., U.S. Pat. No. 5,017,619, Lecount et al., European Patent 427480 and Bloom et al., European Patent 455006.

Even though these more recent developments purport to describe compounds with greater $\beta_3$ selectivity over the $\beta_1$ and $\beta_2$ activities, this selectivity was determined using rodents, in particular, rats as the test animal. Because even the most highly selective compounds, as determined by these assays, still show signs of side effects due to residual $\beta_1$ and $\beta_2$ agonist activity when the compounds are tested in humans, it has become apparent that the rodent is not a good model for predicting human $\beta_3$ selectivity.

Recently, assays have been developed which more accurately predict the effects that can be expected in humans. These assays utilize cloned human $\beta_3$ receptors which have been expressed in Chinese hamster ovary cells. See J.G. Granneman et al., *Mol. Pharmacol.*, 1992, 42:964–970; Emorine et al., *Science*, 1989, 245:1118–1121; and Liggett, *Mol. Pharmacol.*, 1992, 42:634–637. The agonist and antagonist effects of the various compounds on the cultivated cells provide an indication of the antiobesity and antidiabetic effects of the compounds in humans.

SUMMARY OF THE INVENTION

The instant invention is concerned with compounds of Formula I

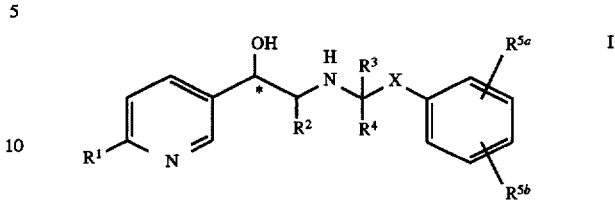

which are useful as antiobesity and antidiabetic compounds. Thus, it is an object of this invention to describe such compounds. It is a further object to describe the specific preferred stereoisomers of the compounds of Formula I. A still further object is to describe processes for the preparation of such compounds. Another object is to describe methods and compositions which use the compounds as the active ingredient thereof. Further objects will become apparent from reading the following description.

DESCRIPTION OF THE INVENTION

The present invention provides compounds having the Formula I:

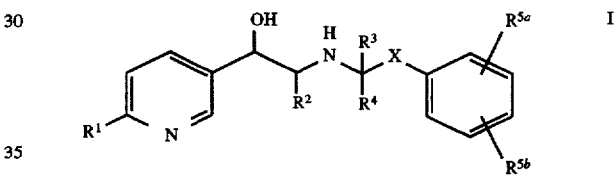

and the pharmaceutically acceptable salts, hydrates and stereoisomers thereof wherein:

X is a bond or is selected from $(CH_2)_n$—, —CH(CN)—,

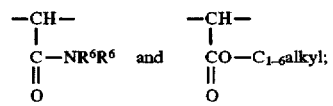

n is selected from 1, 2 and 3;
m is selected from zero, 1, 2 and 3;
p is selected from zero, 1 and 2;
$R^1$ is selected from
 (1) —H,
 (2) —H,
 (3) halogen,
 (4) —NR⁸R⁸,
 (5) —NR⁸COR⁹,
 (6) —NR⁸COH,
 (7) —NR⁸SO₂R⁹, and
 (8)

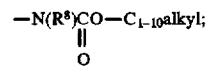

$R^2$ is independently selected at each occurrence from —H and —C₁₋₆ alkyl;

$R^3$ is selected from —H, —$C_{1-12}$ alkyl, heterocycle and

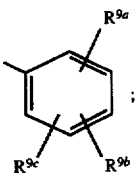

$R^4$ is selected from —H, —$C_{1-12}$ alkyl, —CN, —CONR$^6$R$^6$ and —COOC$_{1-6}$ alkyl;

$R^{5a}$, $R^{5b}$, $R^{9a}$, $R^{9b}$, and $R^{9c}$ are each independently selected from:

(1) —H, —$C_{1-12}$ alkoxy, —$C_{1-6}$ alkyl, halogen, —OH, —CN, —(CH$_2$)$_m$N(R$^2$)COC$_{1-6}$ alkyl, —CON(R$^2$)R$^2$, —CON(R$^2$)OR$^2$, —CO$_2$R$^2$, —S(O)$_p$—C$_{1-6}$ alkyl, —N(R$^2$)SO$_2$R$^7$, —N(R$^2$)R$^2$, —OCH$_2$CON(R$^2$)R$^2$, —OCH$_2$CO$_2$—C$_{1-6}$ alkyl, aryl, —CF$_3$ and —CH$_2$Y wherein Y is selected from —CN, —C$_{1-12}$ alkoxy, —CON(R$^2$)R$^2$, —CO$_2$R$^2$ and —N(R$^2$)SO$_2$R$^7$; or (2) when $R^{5a}$ and $R^{5b}$ are bonded to adjacent carbon atoms, then $R^{5a}$ and $R^{5b}$ together with the carbon atoms to which they are attached may form a phenyl ring or a heterocycle ring, such as for example

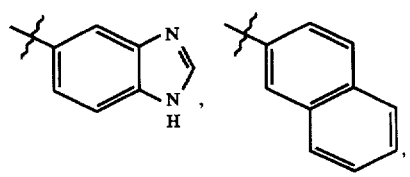

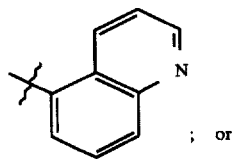; or (3) when $R^{9a}$ and $R^{9b}$ are bonded to adjacent carbon atoms, then $R^{9a}$ and $R^{9b}$ together with the carbon atoms to which they are attached may form a phenyl ring or a heterocycle ring;

$R^6$ is independently selected at each occurrence from: —H, —$C_{1-12}$ alkyl, —$C_{3-6}$ cycloalkyl, aralkyl, aryl and heterocycle, or both R$_6$ groups together with the nitrogen to which they are attached may form a 5–10 membered heterocycle;

$R^7$ is selected from $C_{1-6}$ alkyl, aryl and aralkyl;

$R^8$ is independently selected at each occurrence from —H and $C_{1-10}$ alkyl;

$R^9$ is selected from $C_{1-10}$ alkyl and —NR$^8$R$^8$;

aryl is selected from phenyl, 1-naphthyl and 2-naphthyl and is unsubstituted or mono- or di-substituted, wherein the substituents are independently selected at each occurrence from $R^{5a}$; and heterocycle is an unsubstituted or mono- or di-substituted group selected from:

(1) a 5 or 6-membered saturated or unsaturated heterocyclic ring comprised of carbon atoms and from 1 to 4 heteroatoms independently selected from —O—, —S—, —N—and —NH—, and (2) a benzene ring fused to a saturated or unsaturated 5 or 6-membered heterocyclic ring comprised of carbon atoms and from 1 to 4 heteroatoms independently selected from —O—, —S—, —N—and —NH—, and wherein substituents on the heterocycle are independently selected at each occurrence from nitro, keto, azo, thiazo, and $R^{5a}$.

In one embodiment of the present invention are compounds of Formula I which have the Formula Ia:

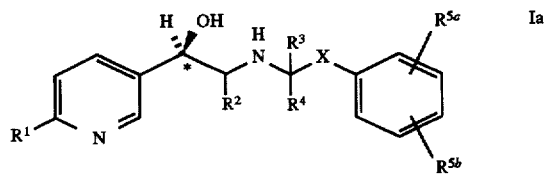

and the pharmaceutically acceptable salts, hydrates and stereoisomers thereof wherein:

X is a bond or is selected from —(CH$_2$)—, —CH(CN)—,

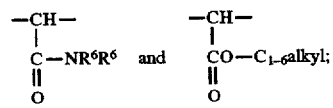

$R^3$ is selected from —H, —$C_{1-12}$ alkyl and

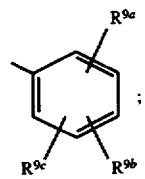

and $R^{5a}$ and $R^{5b}$ are each independently selected from: —H, halogen, —$C_{1-12}$ alkoxy, —$C_{1-6}$ alkyl, —CON(R$^2$)R$^2$ and —CON(R$^2$)OR$^2$.

In a second embodiment of the instant invention are compounds of Formula I which have the Formula Ia:

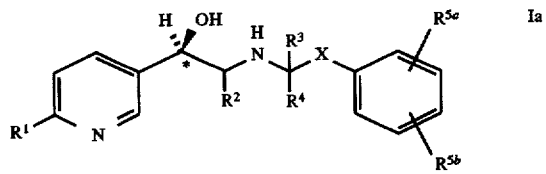

and the pharmaceutically acceptable salts, hydrates and stereoisomers thereof wherein:

X is a bond;

$R^3$ is

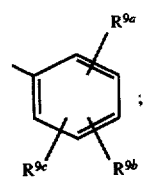

$R^4$ is selected from —H, and —$C_{1-12}$ alkyl; and $R^{5a}$ and $R^{9a}$ are each independently selected from:

(1) —$C^{1-12}$ alkoxy, —OH, —CN, —CON($R^2$)$R^2$, —CON($R^2$)O$R^2$, and —$CH_2Y$ wherein Y is selected from —CN, —$C_{1-12}$ alkoxy, —CON($R^2$)$R^2$, —$CO_2R^2$ and —N($R^2$)$SO_2R^7$; or (2) when $R^{5a}$ and $R^{5b}$ are bonded to adjacent carbon atoms, then $R^{5a}$ and $R^{5a}$ together with the carbon atoms to which they are attached may form a phenyl ring or a heterocycle ring, or (3) when $R^{9a}$ and $R^{9b}$ are bonded to adjacent carbon atoms, then $R^{9a}$ and $R^{9b}$ together with the carbon atoms to which they are attached may form a phenyl ring or a heterocycle ring.

In a third embodiment of the instant invention are compounds of Formula I which have the Formula Ia:

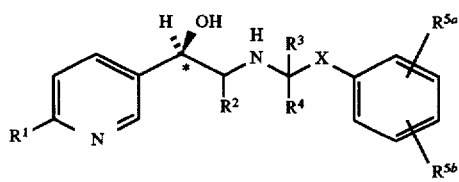

and the pharmaceutically acceptable salts, hydrates and stereoisomers thereof wherein:

X is a bond;

$R^3$ is selected from —H and —$C_{1-12}$ alkyl;

$R^4$ is —CON($R^6$)$R^6$; and $R^{5a}$ is selected from: —$C_{1-12}$ alkoxy, —OH, —CN, —CON($R^2$)$R^2$, and —CON($R^2$)O$R^2$.

In a fourth embodiment of the instant invention are compounds of Formula I which have the Formula Ia:

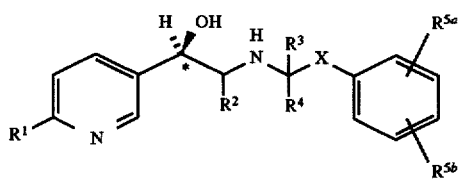

and the pharmaceutically acceptable salts, hydrates and stereoisomers thereof wherein:

X is —($CH_2$)—;

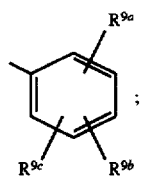

$R^3$ is $R^4$ is selected from —H, —$C_{1-12}$ alkyl, —CN and —CON($R^6$)$R^6$; and $R^{5a}$ is selected from —H, halogen and —$CF_3$; and $R^{9a}$ is selected from (1) —CN, —CON($R^2$)$R^2$, —CON($R^2$)O$R^2$, —OH, —$C_{1-6}$ alkyl and —$C_{1-12}$ alkoxy; or (2) when $R^{9a}$ and $R^{9b}$ are bonded to adjacent carbon atoms, then $R^{9a}$ and $R^{9b}$ together with the carbon atoms to which they are attached may form a phenyl ring or a heterocycle ring.

In a fifth embodiment of the instant invention are compounds of Formula I which have the Formula Ia:

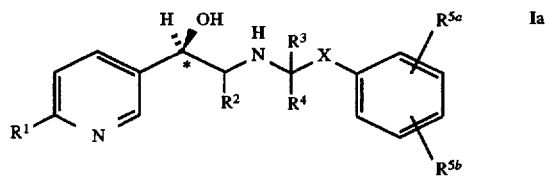

and the pharmaceutically acceptable salts, hydrates and stereoisomers thereof wherein:

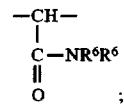

X is selected from —CH(CN)— and $R^3$ and $R^4$ are independently selected from —H and —$C_{1-12}$ alkyl; and $R^{5a}$ is selected from: —$C_{1-12}$ alkoxy, —OH, —CN, —CON($R^2$)$R^2$ and —CON($R^2$)O$R^2$.

In a sixth embodiment of the instant invention are compounds of Formula I wherein:

X is a bond or is selected from —($CH_2$)$_n$—, —CH(CN)—,

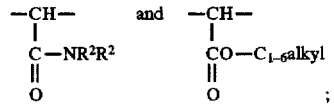

n is selected from 1, 2 and 3;

m is selected from zero, 1, 2 and 3;

p is selected from zero, 1 and 2;

$R^1$ is selected from (1) —H,
(2) —OH,
(3) halogen,
(4) —NR$^8$R$^8$,
(5) —NR$^8$COR$^9$,
(6) —NR$^8$COH,
(7) —NR$^8$SO$_2$R$^9$, and
(8)

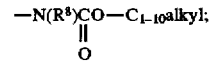

$R^2$ is independently selected at each occurrence from —H and —$C_{1-6}$ alkyl;

$R^3$ is selected from —H, substituted —$C_{1-12}$ alkyl, heterocycle and

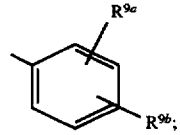

$R^4$ is selected from —H, —$C_{1-12}$ alkyl, —CN, —CON($R^2$)$R^2$ and —COO$C_{1-6}$ alkyl;

$R^{5a}$, $R^{5b}$, $R^{9a}$ and $R^{9b}$ are each independently selected from:

(1) —H, —$C_{1-12}$ alkoxy, —$C_{1-6}$ alkyl, halogen, —OH, —CN, —($CH_2$)$_m$N($R^2$)CO$C_{1-6}$ alkyl, —CON($R^2$)

$R^2$, —$CO_2C_{1-6}$ alkyl, —$S(O)_p$—$C_{1-6}$ alkyl, —$N(R^2)SO_2R^7$, —$N(R^2)R^2$, —$OCH_2CON(R^2)R^2$, and —$OCH_2CO_2$—$C_{1-6}$ alkyl; or (2) when $R^{5a}$ and $R^{5b}$ are bonded to adjacent carbon atoms, then $R^{5a}$ and $R^{5b}$ together with the carbon atoms to which they are attached may form a heterocycle ring, or (3) when $R^{9a}$ and $R^{9b}$ are bonded to adjacent carbon atoms, then $R^{9a}$ and $R^{9b}$ together with the carbon atoms to which they are attached may form a heterocycle ring;

$R^6$ is independently selected at each occurrence from: —H, —$C_{1-12}$ alkyl, —$C_{3-6}$ cycloalkyl, aralkyl, aryl and heterocycle, or both $R^6$ groups together with the nitrogen to which they are attached may form a 5–10 membered heterocycle;

$R^7$ is selected from $C_{1-6}$ alkyl, aryl and aralkyl;

$R^8$ is independently selected at each occurrence from —H and $C_{1-10}$ alkyl;

$R^9$ is selected from $C_{1-10}$ alkyl and —$NR^8R^8$;

aryl is selected from phenyl, 1-naphthyl and 2-naphthyl and is unsubstituted or mono- or di-substituted, wherein the substituents are independently selected at each occurrence from $R^{5a}$; and heterocycle is an unsubstituted or mono- or di-substituted group selected from:

(1) a 5 or 6-membered saturated or unsaturated heterocyclic ring comprised of carbon atoms and from 1 to 4 heteroatoms independently selected from —O—, —S—, —N—and —NH—, and (2) a benzene ring fused to a saturated or unsaturated 5 or 6-membered heterocyclic ring comprised of carbon atoms and from 1 to 4 heteroatoms independently selected from —O—, —S—, —N—and —NH—, and wherein substituents on the heterocycle are independently selected at each occurrence from nitro, keto, azo, thiazo, and $R^{5a}$.

Representative compounds of the present invention include but are not limited to the following:

N-[1-(3,4)-dimethoxyphenyl)-2-phenylethyl]-2-hydroxy-2-pyridin-3-yl-ethylamine;

N-[1-(3,4)-dimethoxyphenyl)-2-phenylethyl]-2-hydroxy-2-(chloropyrid-5-yl)-ethylamine;

α-[[[(R)-2-hydroxy-2-(pyridin-3-yl)ethyl]amino]methyl]-N,N-dimethylbenzeneacetamide;

α-[[[(R)-2-hydroxy-2-(2-chloropyrid-5-yl) ethyl]amino]methyl]-N,N-dimethylbenzeneacetamide;

(R)-N-[1-(3,4)-dimethoxyphenyl)-2-phenylethyl]-2-hydroxy-2-(chloropyrid-5-yl)-ethylamine;

(R)-N-[1-(3,4)-dimethoxyphenyl)-2-phenylethyl]-2-hydroxy-2-pyridin-3-yl-ethylamine;

(R),(R)-N-[1-(3,4)-dimethoxyphenyl)-2-phenylethyl]-2-hydroxy-2-(chloropyrid-5-yl)-ethylamine;

(R),(R)-N-[1-(3,4)-dimethoxyphenyl)-2-phenylethyl]-2-hydroxy-2-pyridin-3-yl-ethylamine;

(R),(S)-N-[1-(3,4)-dimethoxyphenyl)-2-phenylethyl]-2-hydroxy-2-(chloropyrid-5-yl)-ethylamine;

(R),(S)-N-[1-(3,4)-dimethoxyphenyl)-2-phenylethyl]-2-hydroxy-2-pyridin-3-yl-ethylamine;

N-[1-(3,4)-dimethoxyphenyl)-2-phenylethyl]-2-hydroxy-2-(6-aminopyridin-3-yl)-ethylamine; and (R)-N-[1-(3,4)-dimethoxyphenyl)-2-phenylethyl]-2-hydroxy-2-(6-aminopyridin-3-yl)-ethylamine.

Combinations of substituents and/or variables within Formula I are permissible only if such combinations result in stable compounds.

The compounds of the instant invention all have at least one asymmetric center as noted by the asterisk in structural Formula I. Additional asymmetric centers may be present on the molecule depending upon the nature of the various substituents on the molecule, in particular, $R^3$ and $R^4$. Each such asymmetric center will produce two optical isomers and it is intended that all such optical isomers, as separated, pure or partially purified optical isomers or racemic mixtures thereof, be included within the are bit of the instant invention. In the case of the asymmetric center represented by the asterisk in Formula I, it has been found that the compound in which the hydroxy substituent is above the plane of the structure, as seen in Formula Ia, is more active and thus more preferred over the compound in which the hydroxy substituent is below the plane of the structure.

The following stereospecific Structure Ia, wherein $R^1$, $R^2$, $R^3$, $R^4$, $R^{5a}$, $R^{5b}$, and X are as defined in Formula I, represents the preferred stereoisomers of the instant invention:

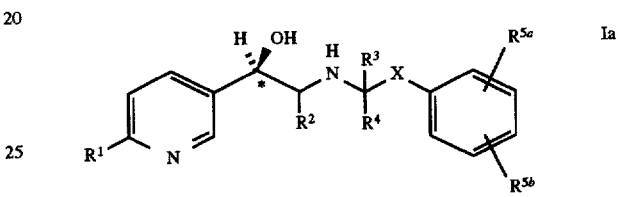

Throughout the instant application, the following terms have the indicated meanings either individually (e.g. alkyl) or as part of a larger group (e.g., as in aralkyl or —$OCH_2CO_2$—$C_{1-6}$ alkyl).

As used herein the terms "alk" and "alkyl" have the same meaning and are intended to include both branched- and straight-chain saturated aliphatic hydrocarbon groups having the specified number of carbon atoms, e.g., methyl (Me), ethyl (Et), propyl (Pr), butyl (Bu), pentyl (Pn), hexyl (hex), heptyl, octyl, nonanyl, decyl, undecyl and dodecyl, and the isomers thereof such as isopropyl (i-Pr), isobutyl (i-Bu), secbutyl (s-Bu), tertbutyl (t-Bu), isopentyl, isohexyl and the like. The terms "alk" and "alkyl" further include both unsubstituted and mono-, di- and tri-substituted hydrocarbon groups as defined above wherein the substituents are independently selected from the group consisting of: halogen (especially to form trihaloalkyl, particularly trichloromethyl or trifluoromethyl), aryl, $C_{3-6}$cycloalkyl, hydroxy, amino, thiol, —CN, $C_{1-12}$ alkoxy, —$CON(R^2)R^2$, —$CO_2R^2$, and —$N(R^2)SO_2R^7$. Alkyl groups of Formula I which are defined as having from 1 to 12 carbon atoms preferably contain from 1 to 8 carbon atoms.

The term "cycloalkyl" is intended to include cyclized alkyl chains having the specified number of carbon atoms, e.g., cyclopropyl, cyclobutyl, cyclopentyl, and cyclohexyl.

"Alkoxy" represents an alkyl group having the indicated number of carbon atoms attached through an oxygen bridge, e.g., methoxy, ethoxy, propyloxy, iso-propoxy, n-butoxy, iso-butoxy, sec-butoxy, t-butoxy and the like.

The terms "halogen" and "halo" have the same meaning and are intended to include the halogen atoms fluorine, chlorine, bromine and iodine.

Aryl is defined above in Formula I. Phenyl and mono- or disubstituted phenyl are preferred.

The term "aralkyl" is intended to mean —$C_{1-12}$ alkyl-aryl, wherein the terms alkyl and aryl are as defined above. In particular, aralkyl includes benzyl (Bz).

Heterocycle is defined above in Formula I. The monocyclic and bicyclic heterocycles described above are unsubstituted, or mono- or di-substituted on any available carbon atoms. The heterocyclic ring may be attached within structural Formula I by any carbon atom or heteroatom, e.g., N, in the ring which results in the creation of a stable structure.

Examples of 5 and 6-membered heterocycles and fused heterocycles include pyridyl, quinolinyl, pyrimidinyl, pyrrolyl, thienyl, imidazolyl, thiazolyl, benzimidazolyl, thiadiazolyl, benzothiadiazolyl, indolyl, indolinyl, benzodioxolyl, benzodioxanyl, benzothiophenyl, benzofuranyl, benzoxazinyl, benzisoxazolyl, benzothiazolyl, tetrahydronaphthyl, dihydrobenzofuranyl, tetrahydroquinolinyl, furopyridine and thienopyridine. Preferred monocyclic heterocycles include 2- and 3-thienyl, 2- and 3-furyl, 2-, 3- and 4-pyridyl, and imidazolyl. Preferred bicyclic heterocycles include 4-, 5-, 6- or 7-indolyl, 4-, 5-, 6- or 7-isoindolyl, 5-, 6-, 7- or 8-quinolinyl, 5-, 6-, 7- or 8-isoquinolinyl, 4-, 5-, 6- or 7-benzothiazolyl, 4-, 5-, 6- or 7-benzoxazolyl, 4-, 5-, 6- or 7-benzimidazolyl, 4-, 5-, 6- or 7-benzoxadiazolyl, 4-, 5-, 6- or 7-benzofuranzanyl, 4-, 5-, 6- or 7-benzodioxolyl, and 4-, 5-, 6- or 7-benzofuran.

Certain of the above defined terms may occur more than once in the above formula and upon such occurrence each term shall be defined independently of the other; thus for example, $N(R^6)R^6$ may represent $NH_2$, $NHCH_3$, $N(CH_3)CH_2CH_3$, and the like.

The compounds of Formula I of the present invention can be prepared from the epoxide intermediates such as those of Formula II and the amine intermediates such as those of Formula III. Preparation of these intermediates is described in the following schemes. The variables used in the schemes (e.g., $R^1$, $R^2$, $R^3$, etc.) are as defined in Formula I unless otherwise noted.

Intermediates II and III are coupled by heating them neat or as a solution in a polar solvent such as methanol, acetonitrile, tetrahydrofuran, dimethylsulfoxide or N-methyl pyrrolidine for 1 to 24 hours at the temperature of 30° to 150° C. to provide compounds I as shown in Scheme 1. The reaction is conveniently conducted in refluxing methanol. Alternately, a salt of amine III, such as the trifluoroacetate or hydrochloride salt, may be used. In these cases, a base such as sodium bicarbonate or diisopropylethylamine is added to the reaction mixture. The product is isolated by recrystallization, trituration, preparative thin layer chromatography, flash chromatography on silica gel as described by W. C. Still, et al., *J. Org. Chem.* 43, 2923 (1978), medium pressure liquid chromatography, or HPLC. Compounds which are purified by HPLC may be isolated as the corresponding salt. Purification of intermediates is achieved in the same manner.

SCHEME 1

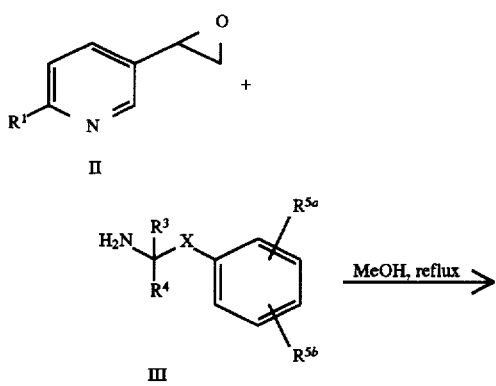

SCHEME 1 -continued

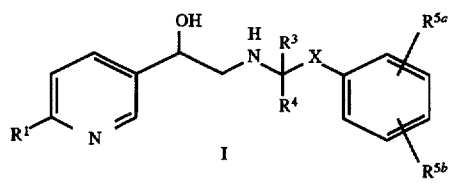

Epoxides of Formula II are known in the literature or may be conveniently prepared by a variety of methods familiar to those skilled in the art. One common route is illustrated in Scheme 2. Acid chloride 1, which may be commercially available or readily prepared from the corresponding acid by treatment with, for example, thionyl chloride or oxalyl chloride, is treated with diazomethane in a solvent such as diethyl ether. The resultant diazoketone is then treated with hydrogen chloride for example to give chloroketone 2 (X=Cl). The haloketone 2 is then reduced with a reducing agent such as sodium borohydride. The resultant alcohol 3 is treated with base such as potassium carbonate in refluxing acetone to provide the desired epoxide II. The enantiomerically enriched (R) and (S) epoxides II are readily available by asymmetric reduction of haloketones 2 using chiral reducing agents such as (−) or (+)-DIP-Cl, (R) or (S)-Alpine borane or (R) or (S)-tetrahydro-1-methyl-3,3-diphenyl-1H,3H-pyrrolo[1,2-c][1,3,2]oxazaborole-borane ((R) or (S)-OAB.BH$_3$).

SCHEME 2

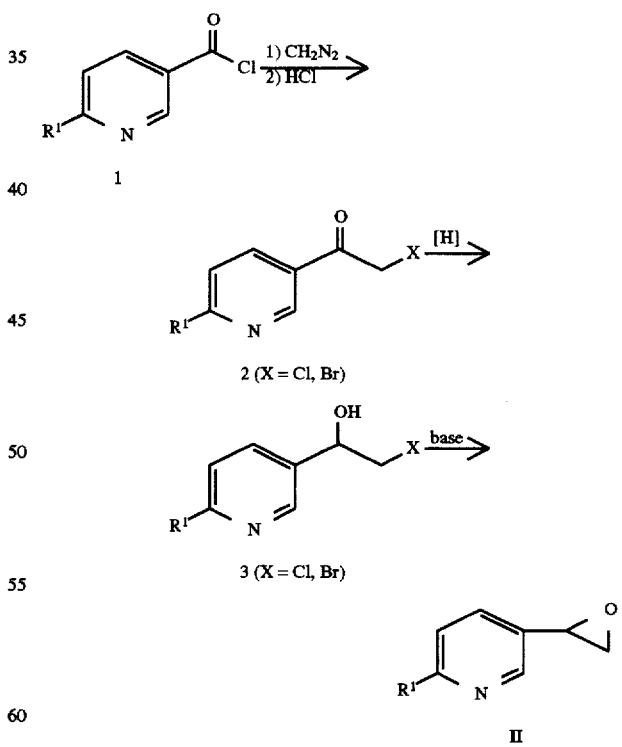

An alternate route to the desired haloketones 2 is illustrated in Scheme 3. Methylketone 4 may be converted to the corresponding haloketone using a variety of reagents known to those in the art and summarized in Larock *Comprehensive Organic Transformations*; VCH: New York, 1989, 369–372.

Conveniently, methylketone 4 is treated with chlorine or N-chlorosuccinimide in acetic acid with an additional acid source such as hydrogen chloride or aluminum chloride. For the synthesis of 2 wherein X=Br, bromine, dibromobarbituric acid or NBS with hydrogen bromide or aluminum bromide may be used. In some cases, the chloro or bromoketones 2 may be commercially available.

SCHEME 3

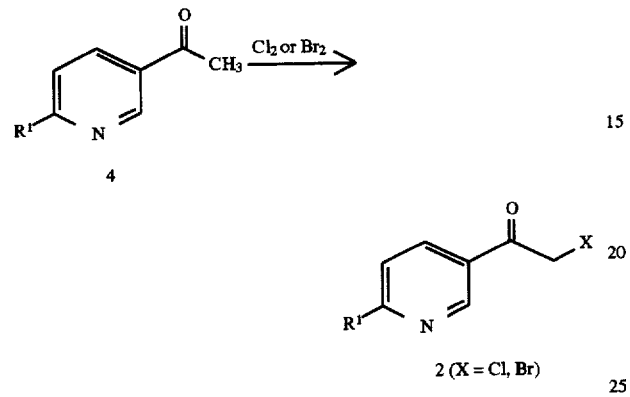

2 (X = Cl, Br)

Many of the methylketones 4 are commercially available or readily prepared by methods described in the literature and known to those skilled in the art. When $R^1$ is —$NH_2$ on the acid chloride 1 or methylketone 4 it may need to be protected during the subsequent procedures. A description of such protecting groups may be found in: *Protective Groups in Organic Synthesis*, 2nd Ed., T. W. Greene and P. G. M. Wus, John Wiley and Sons, New York, 1991.

Preparation of compounds of Formula is described by Washburn, et al in European Patent application 0 659 737 A2 (published Jun. 28, 1995) and references cited therein. An example is illustrated in Scheme 4 for the preparation of intermediate amine 9 (compound III wherein $R^3$=phenyl and $R^4$=H). The appropriate aldehyde 5 in a solvent such as tetrahydrofuran or diethyl ether is reacted with an organometalic reagent 6 to generate the corresponding alcohol which upon treatment with an oxidant such as chromic acid in solvent such as aqueous acetone gives compound 7. The ketone group is convened to an O-alkyl or O-benzyl oxime, conveniently by treatment with O-alkyl or O-benzyl hydroxyamine hydrochloride in ethanol at reflux in the presence of a base such as pyridine or triethylamine. Reduction of oxime ethers 8 with a reducing agent such as diborane gives the amine 9. Optically active compounds of Formula III can be obtained by reduction of oxime ethers 8 with a preequilibriated complex of the borane and enantiomerically pure norephedrine following the method of Y. Sakito et al., *Tet Lett.*, 29, 223 (1988).

SCHEME 4

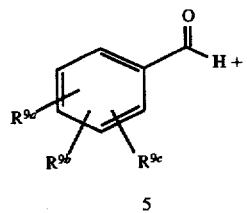

-continued
SCHEME 4

In some cases, the compound produced from the reaction of the intermediate epoxide and the intermediate amine may be further modified to form compounds within Formula I, for example, by the removal of protecting groups or the manipulation of substituents, in particular, the $R^1$ substituent. In addition, manipulation of substituents on any of the intermediates in the reaction sequence illustrated in Scheme 1 may occur. One such example is illustrated in Scheme 5. Compound 10 which is prepared as outlined in Scheme 1 from the corresponding epoxide, is subjected to reduction using Tin II chloride to provide compound 11. Other examples of the substituents on Compound I which may be reduced to the corresponding amine by methods commonly known to those skilled in the art include nitro groups, nitriles, and azides.

SCHEME 5

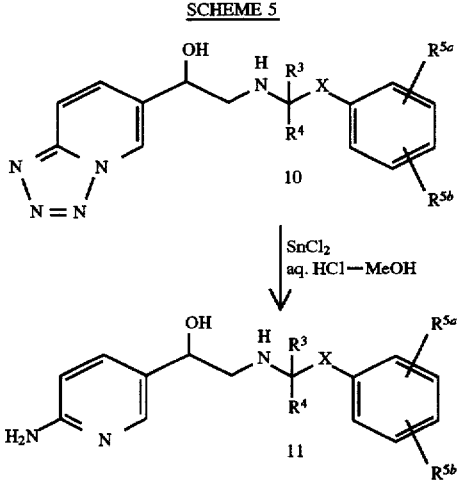

The Compounds I of the present invention can also be prepared from amine intermediates such as those of Formula III and haloketone intermediates such as those of Formula 2 as shown in Scheme 6. Amine III is alkylated with haloketone derivative 2, conveniently by treatment of a mixture of III and 2 in the presence of base such as potassium carbonate or triethylamine in a polar solvent such as acetonitrile, acetone or dimethylformamide. The resulting aminoketone 12 is reduced with a hydrogen source such as sodium borohydride in ethanol to give the desired aminoalcohol I.

SCHEME 6

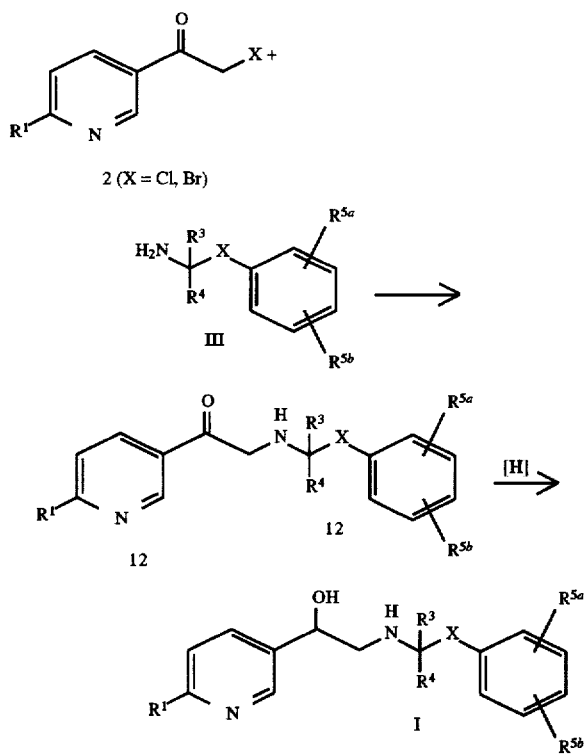

In some cases, the product I from the reaction described in Scheme 6 may be further modified, for example, by removal of protecting groups or the manipulation of substituents, in particular the $R^1$ substituent. These manipulations may include, but are not limited to, reduction, oxidation, alkylation, acylation, and hydrolysis reactions which are commonly known to those skills in art.

An alternate synthesis of compounds of Formula I is illustrated in Scheme 7. The alcohol intermediate 3 is protected, for example, as its t-butyldimethylsilyl ether to give TBS derivative 13. This compound is then treated with amine 111 and a base such as diisopropylethylamine in a solvent, typically polar aprotic such as acetonitrile, at temperature s of 25° to 150° C. for 1 to 72 hours. Typically, an iodide source such as sodium iodide is added to facilitate the reaction. The protecting group is then removed, in the cases of silyl ether, by treatment of the resulting amine 14 with a fluoride source such as tetrabutylammonium fluoride.

SCHEME 7

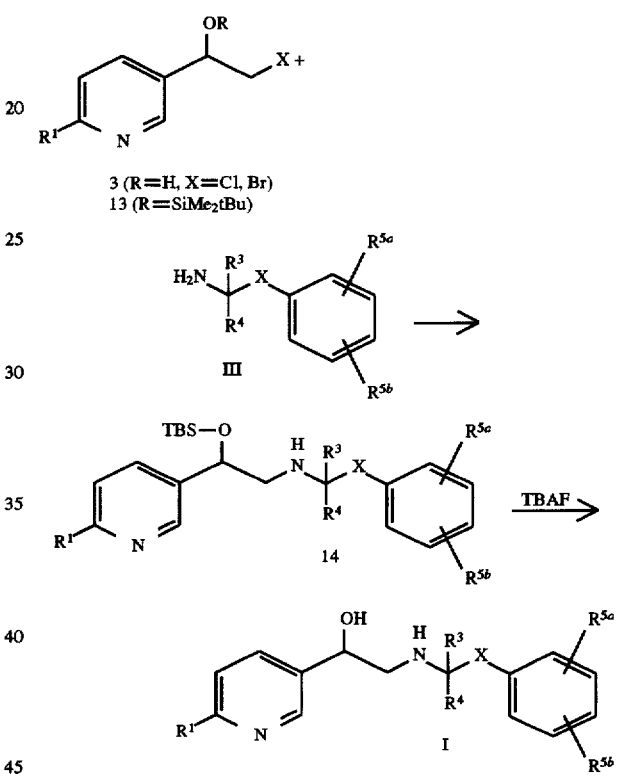

Compounds of the general Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I may be obtained by stereospecific synthesis using optically pure starting materials of known configuration.

The instant compounds can be isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. In addition, certain compounds containing an acidic function such as a carboxy, can be isolated in the form of their inorganic salt in which the counterion can be selected from sodium, potassium, lithium, calcium, magnesium and the like, as well as from organic bases. In addition, the instant invention also encompasses prodrug forms of the compounds of Formula I where such forms can be made. For example, prodrug forms may include pharmaceutically acceptable esters of Formula I compounds which contain an available hydroxy or carboxy group.

The present invention provides a compound of Formula I for use as an active therapeutic substance. In one aspect, the present invention provides a compound of Formula I for use in the treatment of obesity in human or no-n human animals. The present invention further provides a compound of Formula I for use in the treatment of hyperglycemia (diabetes) in human or non human animals.

The disease diabetes mellitus is characterized by metabolic defects in production and utilization of glucose which result in the failure to maintain appropriate blood sugar levels. The result of these defects is elevated blood glucose or hyperglycemia. Research on the treatment of diabetes has centered on attempts to normalize fasting and postprandial blood glucose levels. Treatments have included parenteral administration of exogenous insulin, oral administration of drugs and dietary therapies.

Two major forms of diabetes mellitus are now recognized. Type I diabetes, or insulin-dependent diabetes, is the result of an absolute deficiency of insulin, the hormone which regulates glucose utilization. Type II diabetes, or insulin-independent diabetes, often occurs in the face of normal, or even elevated levels of insulin and appears to be the result of the inability of tissues to respond appropriately to insulin. Most of the Type II diabetics are also obese.

In addition the compounds of the present invention lower triglyceride levels and cholesterol levels and raise high density lipoprotein levels and are therefore of use in combatting medical conditions wherein such lowering (and raising) is thought to be beneficial. Thus they may be used in the treatment of hyper-triglyceridaemia, hypercholesterolaemia and conditions of low HDL (high density lipoprotein) levels in addition to the treatment of atherosclerotic disease such as of coronary, cerebrovascular and peripheral arteries, cardiovascular disease and related conditions.

Accordingly, in another aspect the present invention provides a method of lowering triglyceride and/or cholesterol levels and/or increasing high density lipoprotein levels which comprises administering, to a human or a non-human animal in need thereof, a therapeutically effective amount of a compound of the Formula (I) or pharmaceutically acceptable salt thereof. In a further aspect the present invention provides a method of treating atherosclerosis which comprises administering, to an animal in need thereof; a therapeutically effective amount of a compound of the Formula (I) or pharmaceutically acceptable salt thereof. The compositions are formulated and administered in the same general manner as detailed below for treating diabetes and obesity and they may also contain other active agents known for use in the treatment of atherosclerosis and related conditions.

The compounds of Formula I may be administered in combination with other therapeutically active agents known for use in the treatment of atherosclerosis and related conditions, for example fibrates such as clofibrate, bezafibrate and gemfibrozil; inhibitors of cholesterol biosynthesis such as HMG-CoA reductase inhibitors for example lovastatin, simvastatin, pravastatin and fluvastatin; HMG-CoA-synthase inhibitors, squalene epoxidase inhibitors and squalene synthase inhibitors; inhibitors of cholesterol absorption for example beta-sitosterol and (acyl CoA:cholesterol acyltransferase) inhibitors for example melinamide; anion exchange resins for example cholestyramine, colestipol or a dialkylaminoalkyl derivatives of a cross-linked dextran; nicotinyl alcohol, nicotinic acid or a salt thereof; vitamin E; thyromimetics; and niacin; and probucol.

For combination treatment with more than one active agent, where the active agents are in separate dosage formulations, the active agents can be administered concurrently, or they each can be administered at separately staggered times.

The compounds of the instant invention also have the effect of reducing intestinal motility and thus find utility as aiding in the treatment of various gastrointestinal disorders such as irritable bowel syndrome. It has been proposed that the motility of non-sphincteric smooth muscle contraction is mediated by activity at $\beta_3$ adrenoreceptors. The availability of a $\beta_3$ specific agonist, with little activity at $\beta_1$ and $\beta_2$ receptors will assist in the pharmacologic control of intestinal motility without concurrent cardiovascular effects. The instant compounds are administered generally as described below with dosages similar to those used for the treatment of diabetes and obesity.

It has also been found unexpectedly that the compounds which act as agonists at $\beta_3$ adrenoreceptors may be useful in the treatment of gastrointestinal disorders, especially peptic ulcerations, esophagitis, gastritis and duodenitis, (including that induced by $H.$ $pylori$), intestinal ulcerations (including inflammatory bowel disease, ulcerative colitis, Crohn's disease and proctitis) and gastrointestinal ulcerations.

In addition, $\beta_3$ receptors have been indicated to have an effect on the inhibition of the release of neuropeptides in certain sensory fibers in the lung. As sensory nerves may play an important role in the neurogenic intimation of airways, including cough, the instant specific $\beta_3$ agonists may be useful in the treatment of neurogenetic inflammation, such as asthma, with minimal effects on the cardio-pulmonary system.

$\beta_3$ adrenoreceptors are also able to produce selective antidepressant effects by stimulating the $\beta_3$ receptors in the brain and thus an additional contemplated utility of the compounds of this invention are as antidepressant agents.

The active compounds of the present invention may be orally administered as a pharmaceutical composition, for example, with an inert diluent, or with an assimilable edible carrier, or they may be enclosed in hard or soft shell capsules, or they may be compressed into tablets, or they may be incorporated directly with the food of the diet. For oral therapeutic administration, which includes sublingual administration, these active compounds may be incorporated with excipients and used in the form of tablets, pills, capsules, ampules, sachets, elixirs, suspensions, syrups, and the like. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The effective dosage of active ingredient employed may vary depending on the particular compound employed, the mode of administration, the condition being treated and the severity of the condition being treated.

When treating diabetes mellitus and/or hyperglycemia generally satisfactory results are obtained when the compounds of the present invention are administered at a daily dosage of from about 0.001 milligram to about 10 milligram per kilogram of animal body weight, preferably given in a single dose or in divided doses two to six times a day, or in sustained release form. In the case of a 70 kg adult human, the total daily dose will generally be from about 0.07 milligrams to about 700 milligrams. This dosage regimen may be adjusted to provide the optimal therapeutic response.

When treating obesity, in conjunction with diabetes and/or hyperglycemia, or alone, generally satisfactory results are obtained when the compounds of the present invention are administered at a daily dosage of from 0.01 milligram to about 100 milligrams per kilogram of animal body weight, preferably given in a single dose or in divided doses two to six times a day, or in sustained release form. In the case of a 70 kg adult human, the total daily dose will generally be from about 0.7 milligrams to about 7000 milligrams. This dosage regimen may be adjusted to provide the optimal therapeutic response.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carried such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The following examples are provided so that the invention might be more fully understood. They should not be construed as limiting the invention in any way.

EXAMPLE 1

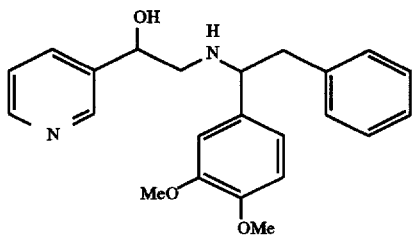

Preparation of N-[1-(3,4-dimethoxyphenyl)-2-phenylethyl]-2-hydroxy-2-pyridin-3-yl-ethylamine Step A: N-[1-(3,4-dimethoxy-phenyl)-2-phenylethyl]-2-hydroxy-2-(2-chloropyrid-5-yl)-ethylamine.

To a solution of α-(3,4-dimethoxyphenyl)-benzeneethanamine (see Washburn et al., EP 0 659 737 A2 for the preparation of this compound) (257 mg, 1 mmol, 2 eq) in anhydrous acetonitrile (10 mL) is added a solution of 2-chloro-5-(2-bromoacetyl)pyridine (prepared as described in Example 3) (111 mg, 0.5 mmol) at 0° C. under a nitrogen atmosphere. The mixture is allowed to warm to room temperature and stirred for 1 h. To this mixture is added a solution of sodium borohydride (110 mg, 2.9 mmol, 5.8 eq) in abs. ethanol at room temperature. After one hour, the excess sodium borohydride is quenched with 1N HCl to pH 4.0 and then ethanol amine (0.28 mL, 4.5 mmol, 8 eq) is added. After stirring for 10 minutes, the mixture is diluted with ethyl acetate (30 mL). The organic layer is washed with brine, dried over anhydrous sodium sulfate and then concentrated. Purification by silica column gives the desired compound.

Step B: N-[1-(3,4-Dimethoxyphenyl)-2-phenylethyl]-2-hydroxy-2-(pyridin-3-yl)-ethylamine A solution of N-[1-(3,4-dimethoxyphenyl)-2-phenylethyl]-2-hydroxy-2-(2-chloropyrid-5-yl)-ethylamine (100 mg, 0.26 mmol) in ethanol (7 mL) with 5N sodium hydroxide (0.1 mL, 0.5 mmol) is degassed with argon prior to addition of Ni(R) (100 mg). The mixture is hydrogenated at 40 Psi for overnight and then the catalyst is filtered through Celite and washed with a small amount of ethanol. Evaporation of the filtrate gives the title compound.

EXAMPLE 2

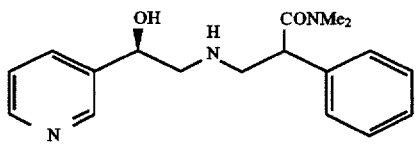

Preparation of α-[[[(R)-2-hydroxy-2-(pyridin-3-yl)ethyl]amino]-methyl]-N,N-dimethylbenzeneacetamide Step A: α-[[[(R)-2-hydroxy-2-(2-chloropyrid-5-yl)ethyl]amino]-methyl]-N,N-dimethylbenzeneacetamide A solution of α-(aminomethyl)-N,N-dimethylbenzacetamide (see Washburn et al., EP 0 659 737 A2 for the synthesis of this starting material) (384 mg, 2 mmol, 2 eq) and (R)-(2-chloropyrid-5-yl)oxirane (prepared as described in Example 3) (143 mg, 1 mmol) in dry methanol in a gas tight vessel is heated in an oil bath at 90° C. overnight. The solvent is stripped and the product is isolated by silica column.

Step B: α-[[[(R)-2-hydroxy-2-(pyridin-5-yl)ethyl]amino]methyl]-N,N-dimethylbenzeneacetamide The title compound is prepared by utilizing the procedure described in Step B of Example 1.

EXAMPLE 3

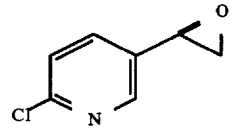

Preparation of (R)-(2-chloropyrid-5-yl)oxirane
Step A: 2-Chloro-5-(2-bromoacetyl)pyridine

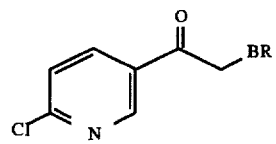

A solution of 784 mg of 2-chloro-5-acetylpyridine in 10 mL of tetrahydrofuran (THF) was added via canula to a solution of 1.44 g of dibromobarbituric acid (DBBA) in 10 mL of THF. The resultant solution was heated at 50°–55° C. for 12 h, and then an additional 0.72 g DBBA was added. After stirring at 50°–55° C. for 2.5 more hours, 0.36 g DBBA was added. The mixture was allowed to stir for 2 h at which point NMR analysis of an aliquot indicated 87% conversion. The reaction mixture was cooled, diluted with ethyl acetate, washed with two portions of saturated aqueous sodium bicarbonate, water, and brine, dried over magnesium sulfate and concentrated. Purification by flash chromatography (silica gel, 15% ethyl acetate/hexane) provided the desired compound as a white solid: $^1$H NMR (400 MHz, CDCl$_3$)δ 8.96 (d, 1H, J=2.6 Hz), 8.21 (dd, 1H, J=2.5, 8.3 Hz), 7.46 (d, 1H, J=8.4 Hz), 4.37 (s, 2H).

Step B: (R)-α-Bromomethyl-3-(6-chloropyridine)methanol

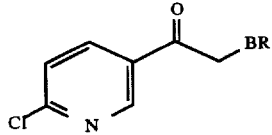

To a solution of 602 mg (1.88 mmol) of (−)-DIP-Cl (diisopinocampheylchloroborane) in 0.5 mL of THF at −25° C. was added via canula 200 mg of ketone from Step A in 1.5 mL of THF at −25° C. The reaction mixture was allowed to stir at −25° C. for 17 h. It was then quenched by the addition of water and extracted with ether. The ether phase was diluted with ethyl acetate, washed with two portions of saturated aqueous sodium bicarbonate, water, and brine, dried over magnesium sulfate and concentrated. Purification by flash chromatography (silica gel, 15 and 25% ethyl acetate/hexane) gave the desired compound: $^1$H NMR (400 MHz, CDCl$_3$)δ 8.38 (d, 1H), 7.70 (dd, 1H), 7.32 (d, 1H), 4.97 (m, 1H), 3.61 (dd, 1H), 3.50 (dd, 1H), 2.85 (d, 1H).

Step C: (R)-(2-chloropyrid-5-yl)oxirane

To a solution of 100 mg of bromoalcohol from Step B in 2 mL of 1:1 THF:water was added 1 mL of 5N aqueous sodium hydroxide solution. The mixture was allowed to stir for 10 min. It was then extracted with three portions of dichloromethane. The combined organic phases were washed with two portions of water and brine, dried over magnesium sulfate, and concentrated to give the title compound: $^1$H NMR (400 MHz, CDCl$_3$)δ 8.34 (d, 1H), 7.48 (dd, 1H), 7.29 (d, 1H), 3.86 (dd, 1H), 3.18 (dd, 1H), 2.78 (dd, 1H).

EXAMPLE 4

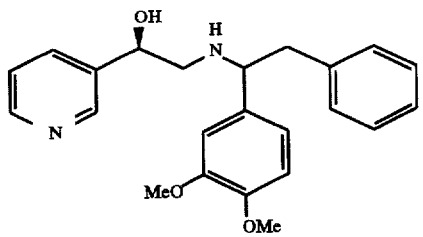

Preparation of (R)-N-[1-(3,4-Dimethoxyphenyl)-2-phenylethyl]-2-hydroxy-2-pyridin-3-yl-ethylamine Step A: (R)-N-[1-(3,4-Dimethoxyphenyl)-2-phenylethyl]-2-hydroxy-2-(2-chloropyrid-5-yl)-ethylamine A solution of α-(3,4-dimethoxyphenyl)benzeneethanamine (257 mg, 1 mmol, 2 eq) and (R)-(2-chloropyrid-5-yl)oxirane (Example 3, 77 mg, 0.5 mmol) in dry methanol in a gas tight vessel was heated at reflux in an oil bath overnight. The reaction was cooled to room temperature and then the solvent was stripped under vacuum. The yellow residue was purified by flash chromatography on silica gel (eluent: ethylacetate: hexanes:9:1) to give the adduct as a white solid. $^1$H NMR (400 MHz, CDCl$_3$)δ 8.20 (m, 1H), 7.53 (m, 1H), 7.07–7.30 (m, 6H), 6.71–6.8 (m, 3H), 4.38–4.58 (m, 1H), 3.87 and 3.86 (s, 3H, OCH$_3$), 3.82 (s, 3H, OCH$_3$), 3.70–3.85 (m, 1H), 2.80–3.0 (m, 2H), 2.64–2.73 (m, 1H), 2.35–2.51 (m, 1H).

Step B: (R)-N-[1-(3,4-Dimethoxyphenyl)-2-phenylethyl]-2-hydroxy-2-(pyridin -3-yl)-ethylamine A solution of (R)-N-[1-(3,4-dimethoxyphenyl)-2-phenylethyl]-2-hydroxy-2-(2-chloropyrid-5-yl)-ethylamine (100 mg, 0.26 mmol) in ethanol (7 mL) with 5N sodium hydroxide (0.1 mL, 0.5 mmol) was degassed with argon prior to the addition of Ni(R) (100 mg). The mixture was hydrogenated at 40 Psi overnight and then the catalyst was filtered through Celite and washed with a small amount of ethanol. The filtrate was stripped and the product was purified by prep TLC on silica gel (eluent: 5% methanol in methylene chloride) to give the titled compound. $^1$H NMR (500 MHz, CDCl$_3$)δ 8.47 (m, 2H), 7.58 (m, $^1$H), 7.01–7.32 (m, 6H), 6.79–6.84 (m, 3H), 4.53–4.67 (m, 1H), 3.89 and 3.88(s, 3H, OCH$_3$), 3.86 (s, 3H, OCH$_3$), 3.79–3.85 (m, 1H), 2.90–3.03 (m, 2H), 2.78 (m, 1H), 2.49–2.50 (m, 1H).

EXAMPLE 5

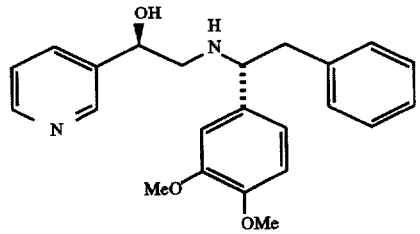

Preparation of (R),(R)-N-[1-(3,4-Dimethoxyphenyl)-2-phenylethyl]-2-hydroxy-2-(pyridin-3-yl)-ethylamine Following the procedure outlined in Example 4, the title compound was prepared from the epoxide from Example 3 and (R)-α-(3,4-dimethoxyphenyl)benzeneethanamine: $^1$H NMR (500 MHz, CDCl$_3$)δ 8.48 (d, 1H, J=4.8 Hz), 8.46 (s, 1H), 7.57 (dd, 1H, J=4.8, 1.4 Hz), 7.09–7.31 (m, 6H), 6.77–6.83 (m, 3H), 4.49(t, 1H, J=7.2 Hz), 3.88(s, 3H, OCH$_3$), 3.86 (s, 3H, OCH$_3$), 3.78 (m, 1H), 2.88–3.0 (m, 2H), 2.78 (dd, 1H, J=4.8, 3.5 Hz), 2.57 (dd, 1H, J=13, 8 Hz).

EXAMPLE 6

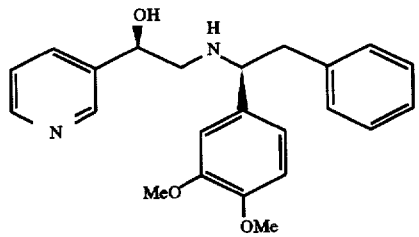

Preparation of (R),(S)-N-[1-(3,4-Dimethoxyphenyl)-2-phenylethyl]-2-hydroxy-2-(pyridin-3-yl)-ethylamine Following the procedure outlined in Example 4, the title compound was prepared from the epoxide from Example 3 and (S)-α-(3,4-dimethoxyphenyl)benzeneethanamine (prepared as described in Example 7): $^1$H NMR (500 MHz, CDCl$_3$)δ 8.48 (m, 2H) 7.57 (d, 1H J=8 Hz), 7.15–7.32 (m, 6H), 6.77–6.84 (m, 3H), 4.62 (dd, 1H, J=9.2, 3.3 Hz), 3.89 (s, 3H, OCH₃), 3.85 (s, 3H, OCH₃), 3.87 (m, 1H), 2.99 (dd, 1H, J=13.5, 5.5 Hz), 2.89 (dd, 1H, J=13.5, 8.5 Hz), 2.73 (dd, 1H, J=11.5, 3.3 Hz), 2.49 (dd, 1H, J=11.5, 9.2 Hz).

EXAMPLE 7

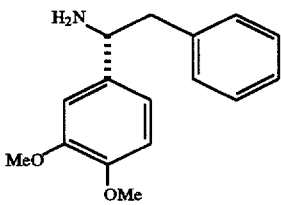

Preparation of (S)-α-(3,4-dimethoxyphenyl) benzeneethanamine

To a cooled (0° C.) solution of (1R,2S)-(−)-norephedrine (2.65 g, 17.5 mmole, 2.5 eq) in anhydrous THF (25 mL) was added BH₃-THF complex (35 mL, 35 mmol, 1.0M solution in THF) dropwise under nitrogen atmosphere. After warming to room temperature and stirring for 20 minutes, a solution of anti-1-(3,4-dimethoxyphenyl)-2-phenylethanone, O-methyloxime (see Washburn et al., EP 0 659 737 A2 for the preparation of this compound) (2 g, 7.34 mmol) in THF (10 mL) was added and then the reaction was refluxed for 2 hours. The reaction was cooled and 1N aq. HCl was added to adjusted the pH to 2.5. The solvent was stripped and the residue was dissolved in water and the solution was basified with 1N aq. NaOH to pH 10. The basic solution was extracted with ether (4×) and the combined organic layer was washed with brine and dried (anhydrous sodium sulfate) and then filtered. The solvent was stripped and the residue was purified by column chromatography on silca gel (eluent 10% hexanes in ethyl acetate) to give the title compound: [α]_D=+69.8 (MeOH). ¹H NMR (400 MHz, CDCl₃) δ 7.14–7.19 (m, 5H), 6.79–6.86 (m, 3H), 4.14 (dd, 1H, J=8.5, 5.1 Hz), 3.85 (s, 3H), 3.84 (s, 3H), 2.95 (dd, 1H, J=13.3, 5.1 Hz), 2.79 (dd, 1H, J=13.3, 8.5 Hz).

EXAMPLE 8

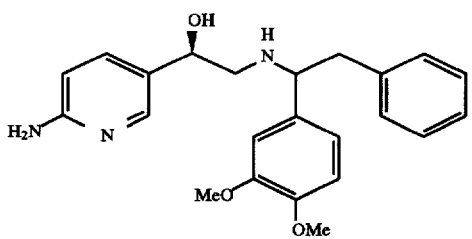

Preparation of (R)-N-[1-(3,4-dimethoxyphenyl)-2-phenylethyl]-2-hydroxy-2-(6-aminopyrin-3-yl)-ethylamine Step A: (R)-N-[1-(3,4-dimethoxyphenyl)-2-phenylethyl]-2-hydroxy-2-(tetrazolo[1,5-a]pyrid-6-yl)-ethylamine A solution of 0.178 g (1 mmol) of (R)-2-(tetrazolo[1,5-a]pyrid-6-yl)oxirane (see Fisher and Wyvratt, EP 0 318 092 A2 for the synthesis of this compound) and 0.518 g (2 mmol) of α-(3,4-dimethoxyphenyl) benzeneethanamine in dry methanol (10 mL) was heated at reflux in a gas tight vessel for 14 hours. The reaction mixture was concentrated and the residue was chromatographed on silica gel (5% methaol in methylene chloride) to give the product as a white solid: ¹H NMR (500 MHz, CDCl₃) δ 8.76 (d, 1H, J=15 Hz), 7.91 (dd, 1H, J=9, 3 Hz), 7.41 (t, 1H, J=11 Hz), 7.10–7.32 (m, 5H), 6.77–6.83 (m, 3H), 4.51–4.73 (m, 1H), 3.89 (s, 3H, OCH₃), 3.88 and 3.86 (s, 3H, OCH₃), 3.74–3.89 (m, 1H), 2.96–3.0 (m, 1H), 2.84–2.92 (m, 2H), 2.94–2.61 (m, 1H).

Step B: (R)-N-[1-(3,4-Dimethoxyphenyl)-2-phenylethyl]-2-hydroxy-2-(6-aminopyrin-3-yl)-ethylamine A mixture of (R)-N-[1-(3,4-Dimethoxyphenyl)-2-phenylethyl]-2-hydroxy-2-(tetrazolo[1,5-a]pyrid-6-yl) ethylamine (104 mg, 0.25 mmol) and tin(II) chloride dihydrate (169 mg, 0.75 mmol, 3 eq) in methanol (5 mL) was heated at reflux for 14 hours. The reaction mixture was concentrated and the residue was dissolved in a small amount of 20% ammonium hydroxide in methanol and then concentrated to dryness. The residue was purified by preparative thin layer chromatography on silica gel (eluent: 10% methanol, 0.5% ammonia/methylene chloride) to give the title compound as a white solid: ¹H NMR (500 MHz, CDCl₃) δ 7.91 (s, 1H), 7.10–7.34 (m, 5H), 6.78–6.84 (m, 3H), 6.43 (dd, 1H, J=8.4, 1.8 Hz), 4.40–4.53 (m, 1H), 3.89 ans 3.88 (s, 3H, OCH₃), 3.86 (s, 3H, OCH₃), 3.78–89 (m, 1H), 2.90–3.0 (m, 2H), 2.63–2.71 (m, 1H), 2.49–2.59 (m, 1H).

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of Formula I

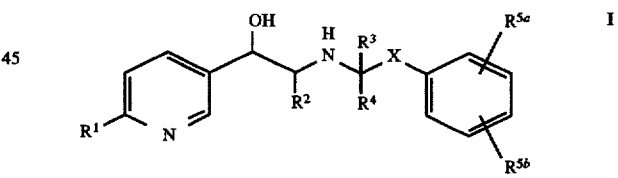

or pharmaceutically acceptable salts, hydrates and stereoisomers thereof wherein:

X is a bond or is selected from —(CH₂)ₙ—, —CH(CN)—,

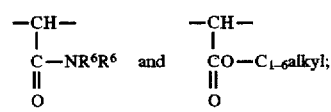

n is selected from 1, 2 and 3;
m is selected from zero, 1, 2 and 3;
p is selected from zero, 1 and 2;
R¹ is selected from
(1) —H,
(2) —OH,
(3) halogen, (4) —NR$^8$R$^8$,
(5) —NR$^8$COR$^9$,
(6) —NR$^8$COH,
(7) —NR$^8$SO$_2$R$^9$, and
(8)

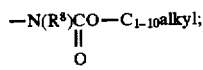
—N(R$^8$)CO—C$_{1-10}$alkyl;

R$^2$ is independently selected at each occurrence from —H and —C$_{1-6}$alkyl;

R$^3$ is selected from —H, —C$_{1-12}$ alkyl, heterocycle and

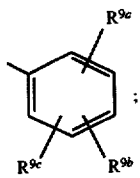

R$^4$ is selected from —H, C$_{1-12}$ alkyl, —CN, —CON(R$^6$) R$^6$ and —COOC$_{1-6}$ alkyl;

R$^{5a}$, R$^{5b}$, R$^{9a}$, R$^{9b}$, and R$^{9c}$ are each independently selected from:

(1) —H, —C$_{1-12}$ alkoxy, —C$_{1-6}$ alkyl, halogen, —OH, —CN, —(CH$_2$)$_m$N(R$^2$)COC$_{1-6}$ alkyl, —CON(R$^2$) R$^2$, —CON(R$^2$)OR$^2$, —CO$_2$R$^2$, —S(O)$_p$—C$_{1-6}$ alkyl, —N (R$^2$)SO$_2$R$^7$, —N(R$^2$)R$^2$, —OCH$_2$CON (R$^2$)R$^2$, —OCH$_2$CO$_2$—C$_{1-6}$ alkyl, aryl, —CF$_3$ and —CH$_2$Y wherein Y is selected from —CN, —C$_{1-12}$ alkoxy, —CON(R$^2$)R$^2$, —CO$_2$R$^2$ and —N(R$^2$)SO$_2$R$^7$; or (2) when R$^{5a}$ and R$^{5b}$ are bonded to adjacent carbon atoms, then R$^{5a}$ and R$^{5a}$ together with the carbon atoms to which they are attached may form a phenyl ring or a heterocycle ring, or (3) when R$^{9a}$ and R$^{9b}$ are bonded to adjacent carbon atoms, then R$^{9a}$ and R$^{9b}$ together with the carbon atoms to which they are attached may form a phenyl ring or a heterocycle ring;

with the proviso that when R$^1$ is NH$_2$ or F, R$^2$ is hydrogen, R$^3$ is methyl, R$^4$ is H or methyl, X is (CH$_2$)$_2$, R$^{5a}$ is hydrogen, then R$^{5b}$ is other than H, OH or methoxy;

R$^6$ is independently selected at each occurrence from: —H, —C$_{1-12}$ alkyl, —C$_{3-6}$ cycloalkyl, aralkyl, aryl and heterocycle, or both R$^6$ groups together with the nitrogen to which they are attached may form a 5–10 membered heterocycle;

R$^7$ is selected from C$_{1-6}$ alkyl, aryl and aralkyl;

R$^8$ is independently selected at each occurrence from —H and C$_{1-10}$ alkyl;

R$^9$ is selected from C$_{1-10}$ alkyl and —NR$^8$R$^8$;

aryl is selected from phenyl, 1-naphthyl and 2-naphthyl and is unsubstituted or mono- or di-substituted, wherein the substituents are independently selected at each occurrence from R$^{5a}$; and heterocycle is an unsubstituted or mono- or di-substituted group selected from:

(1) a 5 or 6-membered saturated or unsaturated heterocyclic ring comprised of carbon atoms and from 1 to 4 heteroatoms independently selected from —O—, —S—, —N— and —NH—, and (2) a benzene ring fused to a saturated or unsaturated 5 or 6-membered heterocyclic ring comprised of carbon atoms and from 1 to 4 heteroatoms independently selected from —O—, —S—, —N— and —NH—, and wherein substituents on the heterocycle are independently selected at each occurrence from nitro, keto, azo, thiazo, and R$^{5a}$.

2. The compound of claim 1 having the Formula Ia

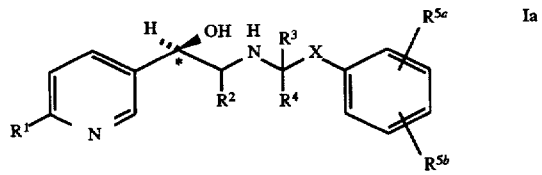

or pharmaceutically acceptable salts, hydrates and stereoisomers thereof wherein:

X is a bond or is selected from —(CH$_2$)—, —CH(CN)—,

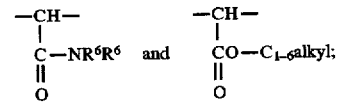

R$^3$ is selected from —H, —C$_{1-12}$ alkyl and

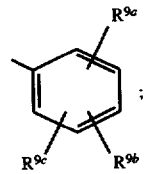

and

R$^{5a}$ and R$^{5b}$ are each independently selected from: —H, halogen, —C$_{1-12}$ alkoxy, —C$_{1-6}$ alkyl, —CON(R$^2$)R$^2$ and —CON(R$^2$)OR$^2$.

3. The compound of claim 1 having the Formula Ia

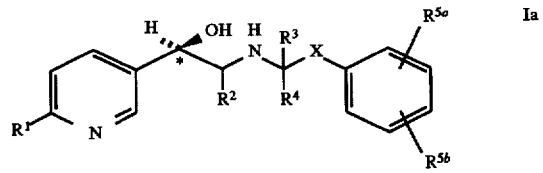

or pharmaceutically acceptable salts, hydrates and stereoisomers thereof wherein:

X is a bond;
R$^3$ is

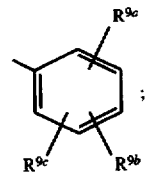

R$^4$ is selected from —H, and —C$_{1-12}$ alkyl; and
R$^{5a}$ and R$^{9a}$ are each independently selected from:

(1) —C$_{1-12}$ alkoxy, —OH, —CN, —CON(R$^2$)R$^2$, —CON(R$^2$)OR$^2$, and —CH$_2$Y wherein Y is selected from —CN, —C$_{1-12}$ alkoxy, —CON(R$^2$)R$^2$, —CO$_2$R$^2$ and —N(R$^2$)SO$_2$R$^7$; or (2) when R$^{5a}$ and R$^{5b}$ are bonded to adjacent carbon atoms, then R$^{5a}$ and R$^{5b}$ together with the carbon atoms to which they are attached may form a phenyl ring or a heterocycle ring, or (3) when $R^{9a}$ and $R^{9b}$ are bonded to adjacent carbon atoms, then $R^{9a}$ and $R^{9b}$ together with the carbon atoms to which they are attached may form a phenyl ring or a heterocycle ring.

4. The compound of claim 1 having the Formula Ia

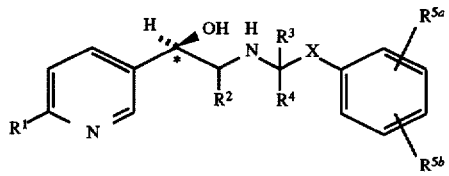

or pharmaceutically acceptable salts, hydrates and stereoisomers thereof wherein:

X is a bond;
$R^3$ is selected from —H and —$C_{1-12}$ alkyl;
$R^4$ is —CON($R^6$)$R^6$; and
$R^{5a}$ is selected from: —$C_{1-12}$ alkoxy, —OH, —CN, —CON($R^2$)$R^2$, and —CON($R^2$)O$R^2$.

5. The compound of claim 1 having the Formula Ia

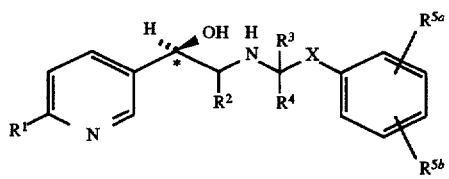

or pharmaceutically acceptable salts, hydrates and stereoisomers thereof wherein:

X is —(CH$_2$)—;

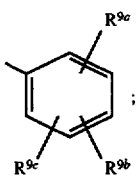

$R^3$ is
$R^4$ is selected from —H, —$C_{1-12}$ alkyl, —CN and —CON($R^6$)$R^6$; and
$R^{5a}$ is selected from —H, halogen and —CF$_3$; and
$R^{9a}$ is selected from
(1) —CN, —CON($R^2$)$R^2$, —CON($R^2$)O$R^2$, —OH, —$C_{1-6}$ alkyl and —$C_{1-12}$ alkoxy; or
(2) when $R^{9a}$ and $R^{9b}$ are bonded to adjacent carbon atoms, then $R^{9a}$ and $R^{9b}$ together with the carbon atoms to which they are attached may form a phenyl ring or a heterocycle ring.

6. The compound of claim 1 having the Formula Ia

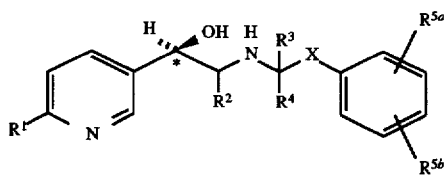

or pharmaceutically acceptable salts, hydrates and stereoisomers thereof wherein:

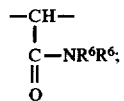

X is selected from —CH(CN)—and
$R^3$ and $R^4$ are independently selected from —H and —$C_{1-12}$ alkyl; and
$R^{5a}$ is selected from: —$C_{1-12}$ alkoxy, —OH, —CN, —CON($R^2$)$R^2$ and —CON($R^2$)O$R^2$.

7. The compound of claim 1 wherein:

X is a bond or is selected from —(CH$_2$)n—, —CH(CN)—,

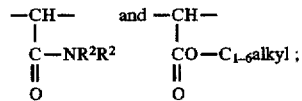

n is selected from 1, 2 and 3;
m is selected from zero, 1, 2 and 3;
p is selected from zero, 1 and 2;
$R^1$ is selected from
(1) —H,
(2) —OH,
(3) halogen,
(4) —NR$^8$R$^8$,
(5) —NR$^8$COR$^9$,
(6) —NR$^8$COH,
(7) —NR$^8$SO$_2$R$^9$, and
(8)

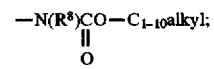

$R^2$ is independently selected at each occurrence from —H and —$C_{1-6}$ alkyl;
$R^3$ is selected from —H, substituted —$C_{1-12}$ alkyl, heterocycle and

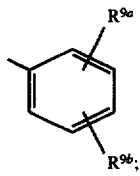

$R^4$ is selected from —H, —$C_{1-12}$ alkyl, —CN, —CON($R^2$)$R^2$ and —COO$C_{1-6}$ alkyl;
$R^{5a}$, $R^{5a}$, $R^{9a}$ and $R^{9b}$ are each independently selected from:
(1) —H, —$C_{1-12}$ alkoxy, —$C_{1-6}$ alkyl, halogen, —OH, —CN, —(CH$_2$)$_m$N(R$^2$)COC$_{1-6}$ alkyl, —CON(R$^2$)R$^2$, —CO$_2$C$_{1-6}$ alkyl, —S(O)$_p$—$C_{1-6}$ alkyl, —N(R$^2$)SO$_2$R$^7$, —N(R$^2$)R$^2$, —OCH$_2$CON(R$^2$)R$^2$, and —OCH$_2$CO$_2$—$C_{1-6}$ alkyl; or
(2) when $R^{5a}$ and $R^{5a}$ are bonded to adjacent carbon atoms, then $R^{5a}$ and $R^{5b}$ together with the carbon atoms to which they are attached may form a heterocycle ring, or
(3) when $R^{9a}$ and $R^{9b}$ are bonded to adjacent carbon atoms, then $R^{9a}$ and $R^{9b}$ together with the carbon atoms to which they are attached may form a heterocycle ring;

with the proviso that when $R^1$ is $NH_2$ or F, $R^2$ is hydrogen, $R^3$ is methyl, $R^4$ is H or methyl, X is $(CH_2)_2$, $R^{5a}$ is hydrogen, then $R^{5b}$ is other than H, OH or methoxy;

$R^7$ is selected from $C_{1-6}$ alkyl, aryl and aralkyl;

$R^8$ is independently selected at each occurrence from —H and $C_{1-10}$ alkyl;

$R^9$ is selected from $C_{1-10}$ alkyl and —$NR^8R^8$;

aryl is selected from phenyl, 1-naphthyl and 2-naphthyl and is unsubstituted or mono- or di-substituted, wherein the substituents are independently selected at each occurrence from $R^{5a}$; and heterocycle is an unsubstituted or mono- or di-substituted group selected from:
(1) a 5 or 6-membered saturated or unsaturated heterocyclic ring comprised of carbon atoms and from 1 to 4 heteroatoms independently selected from —O—, —S—, —N— and —NH—, and
(2) a benzene ring fused to a saturated or unsaturated 5 or 6-membered heterocyclic ring comprised of carbon atoms and from 1 to 4 heteroatoms independently selected from —O—, —S—, —N— and —NH—, and wherein substituents on the heterocycle are independently selected at each occurrence from nitro, keto, azo, thiazo, and $R^{5a}$.

8. A compound of claim 1 selected from the group:

N-[1-(3,4)-dimethoxyphenyl)-2-phenylethyl]-2-hydroxy-2-pyridin-3-yi-ethylamine;

N-[1-(3,4)-dimethoxyphenyl)-2-phenylethyl]-2-hydroxy-2-(chloropyrid-5-yl)-ethylamine;

α-[[[(R)-2-hydroxy-2-(pyridin-3-yl)ethyl]amino]methyl]-N,N-dimethylbenzeneacetamide;

α-[[[(R)-2-hydroxy-2-(2-chloropyrid-5-yl)ethyl]amino]methyl]-N,N-dimethylbenzeneacetamide;

(R)-N-[1-(3,4)-dimethoxyphenyl)-2-phenylethyl]-2-hydroxy-2-(chloropyrid-5-yl)-ethylamine;

(R)-N-[1-(3,4)-dimethoxyphenyl)-2-phenylethyl]-2-hydroxy-2-pyridin-3-yl-ethylamine;

(R),(R)-N-[1-(3,4)-dimethoxyphenyl)-2-phenylethyl]-2-hydroxy-2-(chloropyrid-5-yl)-ethylamine;

(R),(R)-N-[1-(3,4)-dimethoxyphenyl)-2-phenylethyl]-2-hydroxy-2-pyridin-3-yl-ethylamine;

(R),(S)-N-[1-(3,4)dimethoxyphenyl)-2-phenylethyl]-2-hydroxy-2-(chloropyrid-5-yl)-ethylamine;

(R),(S)-N-[1-(3,4)-dimethoxyphenyl)-2-phenylethyl]-2-hydroxy-2-pyridin-3-yl-ethylamine;

N-[1-(3,4)-dimethoxyphenyl)-2-phenylethyl]-2-hydroxy-2-(6-aminopyridin-3-yl)-ethylamine; and (R)-N-[1-(3,4)-dimethoxyphenyl)-2-phenylethyl]-2-hydroxy-2-(6-aminopyridin-3-yl)-ethylamine.

9. A method for the treatment of diabetes which comprises administering to a diabetic patient a therapeutically effective amount of a compound of claim 1.

10. A method for the treatment of obesity which comprises administering to an obese patient a therapeutically effective amount of a compound of claim 1.

11. A method for lowering triglyceride levels and cholesterol levels or raising high density lipoprotein levels which comprises administering to a patient needing lower triglyceride and cholesterol levels or higher high density lipoprotein levels a therapeutically effective amount of a compound of claim 1.

12. A method for treating atherosclerotic disease which comprises administering to a patient in need of such treatment a therapeutically effective amount of a compound of claim 1.

13. A method for decreasing intestinal motility which comprises administering to a patient in need of decreased intestinal motility, a therapeutically effective amount of a compound of claim 1.

14. A method for reducing neurogenic inflammation of airways which comprises administering to a patient in need of reduced neurogenic inflammation, a therapeutically effective amount of a compound of claim 1.

15. A method for treating depression which comprises administering to a depressed patient a therapeutically effective amount of a compound of claim 1.

16. A method for treating gastrointestinal disorders which comprises administering to a patient with gastrointestinal disorders a therapeutically effective amount of a compound of claim 1.

17. A pharmaceutical composition comprising a therapeutically effective amount of a compound of claim 1 and an inert carrier.

* * * * *